US012072316B2

(12) United States Patent
Jimenez Gonzalez et al.

(10) Patent No.: US 12,072,316 B2
(45) Date of Patent: Aug. 27, 2024

(54) METHOD FOR PRODUCING A LENS AND ULTRASOUND DEVICE COMPRISING THE LENS

(71) Applicants: Consejo Superior de Investigaciones Cientificas (CSIC), Madrid (ES); Universitat Politecnica de Valencia, Valencia (ES)

(72) Inventors: Noe Jimenez Gonzalez, Madrid (ES); Francisco Camarena Femenia, Valencia (ES); Sergio Jimenez Gambin, Valencia (ES); Jose Maria Benlloch Baviera, Madrid (ES)

(73) Assignees: Consejo Superior de Investigaciones Cientificas (CSIC), Madrid (ES); Universitat Politecnica de Valencia, Valencia (ES)

( * ) Notice: Subject to any disclaimer, the term of this patent is extended or adjusted under 35 U.S.C. 154(b) by 723 days.

(21) Appl. No.: 17/287,715

(22) PCT Filed: Oct. 21, 2019

(86) PCT No.: PCT/ES2019/070713
§ 371 (c)(1),
(2) Date: Apr. 22, 2021

(87) PCT Pub. No.: WO2020/084181
PCT Pub. Date: Apr. 30, 2020

(65) Prior Publication Data
US 2021/0396712 A1    Dec. 23, 2021

(30) Foreign Application Priority Data
Oct. 22, 2018    (ES) .............................. ES201831022

(51) Int. Cl.
*G01N 29/06* (2006.01)
*A61N 7/02* (2006.01)
(Continued)

(52) U.S. Cl.
CPC ........... *G01N 29/0663* (2013.01); *A61N 7/02* (2013.01); *B29D 11/00009* (2013.01);
(Continued)

(58) Field of Classification Search
CPC ............. G01N 29/0663; G01N 29/221; G01N 29/2437; A61B 2034/2051; Y10T 29/49005
(Continued)

(56) References Cited

U.S. PATENT DOCUMENTS

| 8,102,734 B2 * | 1/2012 | Sliwa | A61B 8/4272 367/140 |
| 2013/0301114 A1 * | 11/2013 | Sangawa | A61B 5/0097 359/305 |
| 2016/0038770 A1 | 2/2016 | Tyler et al. | |

FOREIGN PATENT DOCUMENTS

WO    2017097417 A1    6/2017

OTHER PUBLICATIONS

Marcelino Ferri, "Enhanced 3D-printed holographic acoustic lens for aberration correction of single-element transcranial focused ultrasound", Manuscript, 2018, 1-34.
(Continued)

*Primary Examiner* — Thiem D Phan
(74) *Attorney, Agent, or Firm* — Hayes Soloway PC

(57) ABSTRACT

The invention relates to a method for producing a lens for an ultrasound apparatus, as well as to an apparatus comprising the lens. The method comprises choosing a source point, providing a treatment volume situated inside a bone tissue model, providing a plurality of nodes distributed inside the
(Continued)

treatment volume, and simulating the emission of a spherical wave from each of the nodes. Thus, a simulated wave front is created, in which each spherical wave has an amplitude and a phase, there being at least two nodes with different amplitudes and/or phases. The simulated wave front is received on a receiving surface. On the basis of the processed results, a holographic lens surface is designed, which can generate a wave pattern equivalent to the simulated wave.

19 Claims, 5 Drawing Sheets

(51) Int. Cl.
 *B29D 11/00* (2006.01)
 *G10K 11/30* (2006.01)
 *A61N 7/00* (2006.01)
(52) U.S. Cl.
 CPC ...... *G10K 11/30* (2013.01); *A61N 2007/0004* (2013.01); *A61N 2007/006* (2013.01); *Y10T 29/49005* (2015.01)
(58) Field of Classification Search
 USPC .............................. 29/594, 592.1, 609.1, 846
 See application file for complete search history.

(56) References Cited

OTHER PUBLICATIONS

Zeyu Chen, "3D Printing of Piezoelectric Element for Energy Focusing and Ultrasonic Sensing", Article, 2019, 1-31, vol. 27, Nano Energy.

James L.B. Robertson, "Accurate simulation of transcranial ultrasound propagation for ultrasonic neuromodulation and stimulation", Article, 2017, 1726-1738, Journal of the Acoustical Society of America.

Yangbo Xie, "Acoustic Holographic Rendering with Two-dimensional Metamaterial-based Passive Phased Array", Article, 2016, 1-6, Scientific Reports.

Yun Jing, "Time-reversal transcranial ultrasound beam focusing using a k-space method", Article, 2012, 1-24, vol. 57, No. 4, Physics in Medicine and Biology.

Jerome Gateau, "Transcranial Ultrasonic Therapy Based on Time Reversal of Acoustically Induced Cavitation Bubble Signature", Article, 2009, 1-23, vol. 57, No. 1, IEEE Transactions on Biomedical Engineering.

Gil Navon, "Bypassing absorbing objects in focused ultrasound using computer generated holographic technique", Article, 2011, 6407-6415, vol. 38, No. 12, Medical Physics.

Claire Prada, "The iterative time reversal process: Analysis of the convergence", Article, 1994, 62-71, vol. 97, No. 1, Journal of the Acoustical Society of America.

Gianmarco F. Pinton, "Direct Phase Projection and Transcranial Focusing of the Ultrasound for Brain Therapy", Article, 2012, 1149-1159, vol. 59, No. 6, IEEE Transaction on Ultrasonics, Ferroelectrics and and Frequency Control.

Guillaume Maimbourg, "3D-Printed Adaptive Acoustic Lens as a Disruptive Technology for Transcranial Ultrasound Therapy Using Single-Element Transducers", Paper, 2018, 1-15, vol. 63, Physics in Medicine and Biology.

* cited by examiner

METHOD FOR PRODUCING A LENS AND ULTRASOUND DEVICE COMPRISING THE LENS

CROSS-REFERENCE TO RELATED APPLICATIONS AND PRIORITY

This patent application claims priority from PCT Patent Application No. PCT/ES2019/070713 filed Oct. 21, 2019, which claims priority from Spanish Patent Application No. ES P201831022 filed Oct. 22, 2018. Each of these patent applications are herein incorporated by reference in their entirety.

TECHNICAL FIELD

This invention pertains to the technical field of apparatus used for the interaction with the brain or the treatment of brain diseases, and of methods for obtaining said apparatus.

BACKGROUND OF THE INVENTION

The application of ultrasound through the cranial wall in certain parts of the brain has proven to be useful for performing some treatments, such as ablation of part of the thalamus for the treatment of the essential tremor, for opening the blood-brain barrier and allowing the deposition of medicinal products in a reversible and localized manner, or for neurological stimulation.

One of the drawbacks of these techniques can be seen when trying to precisely determine the exact location in the brain where ultrasound energy is going to be deposited. This is due to intense reflection, refraction, and absorption the ultrasound wave sustains as it hits the cranial wall, which presents not only an acoustic impedance that is much higher than that of water and soft tissues, but is furthermore a very heterogeneous medium. This problem has conventionally been resolved by means of using a multi-element ultrasound emitter, but it is a very expensive and complex method.

US patent document 2016/038770 A1 discloses an apparatus and a method for applying high-intensity focused ultrasound (HIFU) in regions close to the cortex area of the brain with a single-element transducer emitter.

Maimbrough et al. (Maimbourg, G., Houdouin, A., Deffieux, T., Tanter, M., & Aubry, J. F. (2018). 3D-printed adaptive acoustic lens as a disruptive technology for transcranial ultrasound therapy using single-element transducers. *Physics in Medicine & Biology*, 63(2), 025026) discloses the use of passive plastic lenses for configuring the wave front generated by a single-element emitter such that at the output of the lens, the wave front already incorporates the phase that would be desirable to be corrected for purposes of refraction, reflection, and absorption introduced by the cranial wall. Lenses of this type facilitate the introduction of ultrasound energy into the brain and correct aberrations of the cranial wall. It is a more cost-effective system than the system based on the use of a multi-element emitter, however it is not efficient when trying to treat volumes that are greater than the volume of said focus.

Ferri et al. (Ferri, M., Bravo, J. M., Redondo, J., & Sánchez-Pérez, J. V. (2018). Enhanced 3D-printed holographic acoustic lens for aberration correction of single-element transcranial focused ultrasound. *arXiv preprint arXiv:*1805.10007) discloses the use of acoustic lenses obtained by means of 3D-printing to improve the transcranial application of focused ultrasound. The study is centered on improving the numerical simulation providing the changes needed to overcome the absorption phenomena caused by the surface of the cranium. However, it does not represent a substantial improvement with respect to the previous method.

The present invention provides an improvement with respect to these methods, since it allows optimizing current methods and would even avow extending the scope of application.

DISCLOSURE OF THE INVENTION

This problem is solved by means of a method for producing a lens for an ultrasound apparatus according to claim 1 and an ultrasound apparatus according to claim 15. The dependent claims define preferred embodiments of the invention.

Thus, in a first inventive aspect, the invention proposes a method for producing a lens for an ultrasound apparatus, the method comprising the steps of providing a bone tissue model, a soft tissue model surrounded by the bone tissue, and a coupling medium model;

choosing a source point situated inside the coupling medium model;

choosing a predetermined wave frequency and wavelength, the predetermined frequency being comprised between 100 kHz and 20 MHz and the predetermined wavelength being determined by the predetermined frequency and a velocity of propagation of the wave in the coupling medium model;

providing a treatment volume situated inside the bone tissue model;

providing a plurality of nodes distributed inside the treatment volume;

simulating the emission of a spherical wave from each of the nodes of the plurality of nodes, creating a simulated wave front resulting from the superposition of the spherical waves, each spherical wave requiring an amplitude and a phase, there being at least two nodes with different amplitudes and/or phases, each spherical wave having the predetermined frequency;

receiving the simulated wave front on a receiving surface which contains the source point;

processing the results received on the receiving surface;

on the basis of the processed results, designing a holographic lens surface which can generate a wave pattern equivalent to the simulated, time-reversed, wave front when it receives a wave from a planar, single-element emitter situated at the source point with the predetermined wave frequency and wavelength.

By means of this method, it is possible to design a passive lens which, when a wave emitted by a single-element ultrasound emitter goes through it, reproduces a three-dimensional acoustic hologram which corresponds with a volume defined by the conditions imposed in the nodes and is as similar as possible to the treatment volume. An ultrasound distribution which is adapted to a specific area of a brain volume to be treated can thus be achieved.

The plurality of nodes is situated inside the treatment volume. By means of the use of a plurality of nodes distributed inside the treatment volume, an ultrasound beam with three-dimensional variants, such as a curved beam, for example, which has a number of applications in the treatment of brain diseases, can be obtained by using the lens product of the method. Due to the use of the holographic lens product of this production method, some treatments that were carried out with multiple sonications can be achieved by means of a single sonication, using a single-element ultrasound emitter. Due to this simplification in the process and in the materials used, a simpler, more efficient, quicker, and more cost-effective method is obtained.

The predetermined frequency is chosen before starting the method, primarily due to treatment criteria. Said predetermined frequency is set and will be used for simulating the waves starting from the nodes. On the basis of said frequency and the velocity of the wave in the soft tissue model, the wavelength can be calculated, resulting from dividing the velocity of propagation of the wave in the soft tissue model by the frequency.

The fact that there are nodes which generate waves with different amplitudes and/or phases allows adjusting these parameters such that a wave front which is more capable of simulating the final result can be obtained.

In particular embodiments, the plurality of nodes are volumetrically distributed inside the treatment volume.

A volumetric distribution of the nodes allows obtaining a lens which reproduces a much more complex treatment volume in a sufficiently approximate manner because when the nodes are distributed in a volume, it is possible to provide information which cannot be obtained when the nodes are situated along a curve or on a plane, resulting in a better characterized treatment volume.

In particular embodiments, the step of processing the results received comprises dividing the receiving surface into pixels and analyzing the amplitude and phase of the wave received in each pixel. In particular embodiments, the pixel size depends on the predetermined wavelength, and in particular the size of each pixel is a square of $5\lambda/6$ of side, $\lambda$ being the predetermined wavelength. Too large of a pixel size would not be suitable for the analysis of wave magnitudes, since all the information received could not be correctly stored. Conversely, too small of a pixel size could cause problems in production, since each pixel corresponds with a column and if the column has a small base, it can produce resonance in reflection modes at the ultrasound working frequency.

In more particular embodiments, each pixel of the receiving surface is considered as a Fabry-Pérot type resonator which can resonate longitudinally, giving rise to a fragment of the lens, and in the step of designing the holographic lens surface equivalent heights are chosen for each fragment of the lens based on the amplitude and phase of the waves received in each pixel of the receiving surface.

This model is sufficiently precise and suitable for production techniques such as those found today, in which the surface of the lens can be discretized with precision to provide a large number of small pixels working as passive sources, thus being able to create a complex geometry.

In particular embodiments of the method, the step of designing the lens is performed by means of time reversal.

The time reversal method is known to one skilled in the art. Basically, this method, which is based on the principles of reciprocity, time invariance, and linearity of the system, consists of emitting a wave from a node and receiving it on a receiving surface, such that on the basis of the data received on the receiving surface, a wave with the original features can be obtained in the node when waves are emitted with the registered phase features on the receiving surface time-inverted.

As would occur if it had a single node, in the case of the wave front created by several nodes, the receiving surface is divided into pixels. In order to achieve suitable phases of the wave front, each of the pixels is considered as a Fabry-Pérot resonator. The height of the equivalent column can be calculated on the basis of the complex transmission coefficient $$T(x, y) = \frac{2Ze^{-ik_0[d-h(x,y)]}}{2Z\cos[k_L h(x, y)] + i(Z\,|^2 +1)\sin[k_L h(x, y)]}$$

Where d is the distance of the lower part of the lens to the receiving surface, Z is the normalized impedance $Z_L/Z_0$, $Z_L$ is the impedance of the material forming the lens, and $Z_0$ is the impedance of water or of the coupling medium between the lens and the cranium. The value of $h(x, y)$ is the height of the equivalent column in the Fabry-Pérot resonator. On the basis of this expression and the data associated with each pixel, the equivalent heights in each pixel can be calculated.

In particular embodiments, any pair of nodes is separated from one another by a distance of less than $\lambda/2$, $\lambda$ being the predetermined wavelength.

This distribution is sufficient for providing a minimum number of nodes which allows generating data for designing a lens with which a sufficiently precise treatment volume is obtained.

In particular embodiments of the method, in the step of simulating the emission of spherical waves the amplitude of at least two spherical waves is different. In particular embodiments of the method, an amplitude is imposed on each spherical wave which depends on the distance between the node emitting said spherical wave and the receiving surface.

The amplitude of a wave is attenuated, among other reasons, due to the distance travelled by said wave, measured with respect to the point of emission. In particular embodiments of the method according to the invention, it is possible for said distance to be different, therefore adjusting the amplitude of the emitted spherical wave to the particular distance from each of the nodes enables obtaining a more reliable result.

In particular embodiments of the method, the amplitude of each spherical wave is a free parameter, and the method includes the iteration of the steps of simulating the emission of spherical waves, receiving the simulated wave front, and processing the results until obtaining by iteration amplitude values for each spherical wave which give rise to a distribution of sound energy in the treatment volume which exceeds a pre-established target.

In particular embodiments of the method, in the step of simulating the emission of spherical waves the phase of at least two spherical waves is different. In particular embodiments of the method, a phase is imposed on each spherical wave which depends on the distance between the node emitting said spherical wave and the receiving surface.

The phase of a wave is affected by the distance travelled by said wave with respect to the point of emission: for one and the same origin, two points situated at different distances result in the wave with a different phase, unless it so happens that the difference between the distances is equal to the wavelength. Adjusting the phase of the spherical wave emitted to the particular distance from each of the nodes enables obtaining a more reliable result.

In particular embodiments of the method, the phase of each spherical wave is a free parameter, and the method includes the iteration of the steps of simulating the emission of spherical waves, receiving the simulated wave front, and processing the results until obtaining by iteration phase values for each spherical wave which give rise to a distribution of sound energy in the treatment volume which exceeds a pre-established target.

Another way to solve the design of the lens is to leave the amplitude or phase of each spherical wave as a free parameter and iterate the steps of simulating the emission of spherical waves, receiving the simulated wave front, and processing the results until obtaining by iteration length values of the Fabry-Pérot resonator which give rise to a distribution of sound energy in the treatment volume which exceeds a pre-established target. Based on making small modifications in each step of iteration, a more precise result can be obtained.

In particular embodiments of the method, said method further comprises the step of three-dimensionally printing the design of the lens which has been obtained in the corresponding step.

Current three-dimensional printing technology allows the production of lenses with tolerances that are sufficiently narrow so that the part produced can respond in a manner sufficiently suitable for being incorporated and used in an ultrasound emission apparatus.

In particular embodiments, a piezoelectric material is used for producing the lens object of the invention. This allows obtaining a lens the geometry of which is sensitive to the application of a different electrical voltage to each pixel, therefore the geometry thereof may vary, within limits, once constructed, even during the working thereof.

In a second inventive aspect, the invention provides an apparatus comprising a lens produced by means of a method according to the previous inventive aspect.

This apparatus presents a lens designed for modifying the ultrasound beam to focus it on a previously chosen volume inside the cranial cavity of a patient. A simpler and more cost-effective apparatus, which furthermore allows medical applications not disclosed up until now, has thereby been obtained.

This apparatus can be optimal for the low-medium power treatment of structures such as the hippocampus, having a large volume compared with the typical volume of an ultrasound beam, in order to open the blood-brain barrier in a localized region. It can also be optimal for the treatment of regions of the brain for neuronal excitation purposes, producing neurological effects, or for HIFU (high-intensity focalized ultrasound) treatment. This apparatus is also optimal for any application where the ultrasound must go through a barrier to reach the target volume, such as the treatment of internal regions of the knee, through the kneecap, by means of ultrasound. This barrier can be a bone barrier or one consisting of any other material medium providing that the acoustic impedance is different from that of the target volume.

BRIEF DESCRIPTION OF THE DRAWINGS

To complete the description and to better understand the invention, the following set of figures is provided. Said figures are an integral part of the description and illustrate one or more particular examples, which should not be interpreted as restricting the scope of protection of the invention, but rather simple as particular examples of how the invention can be carried out. This set comprises the following figures.

PREFERRED EMBODIMENT OF THE INVENTION

Figure 1:
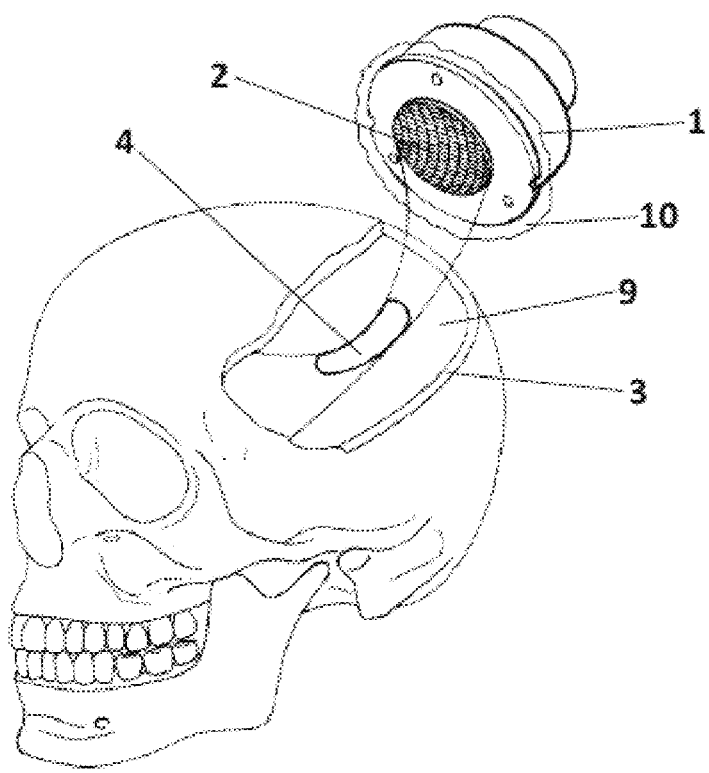
FIG. 1 shows elements that are part of a treatment method for which an apparatus according to the invention is used.

FIG. 1 describes a general approach to a treatment method for which an apparatus according to the invention is used.

An ultrasound emitter 1, a lens 2, and a model cranium 3 are observed in this figure.

The ultrasound emitter 1 consists of a planar or focalized single-element emitter suitable for emitting an ultrasound beam targeting a treatment area 4 situated in a cerebral mass 9 inside the cranial cavity enclosed by the cranium 3. A lens 2, which modifies the ultrasound beam emitted by the ultrasound emitter 1, in order to adapt it to the treatment area 4, is interposed between the emitter 1 and the treatment area 4. The lens is situated inside an aqueous coupling medium 10. In the apparatus and methods known up until now, the treatment area 4 was reduced to an ellipsoid, which is the typical shape of the focus of a conventional ultrasound beam, and no methods or apparatus that could mold or adapt the focus to complex treatment volumes were known.

Figure 2:
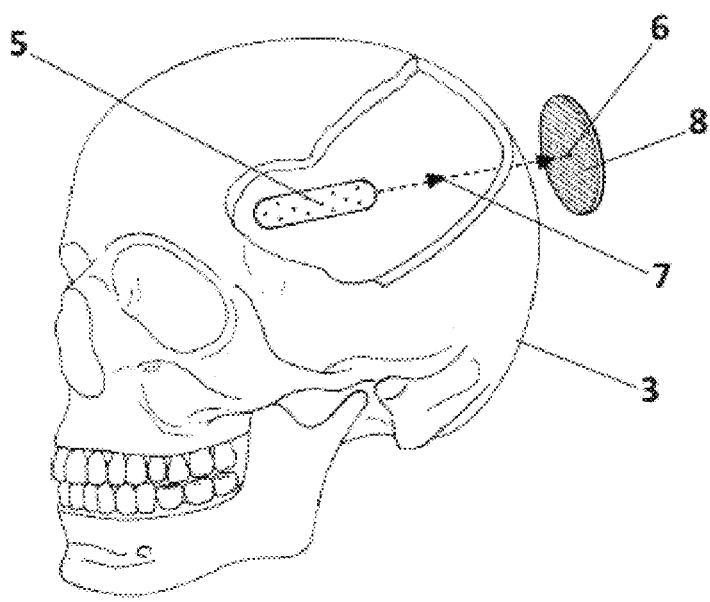
FIG. 2 shows a diagram of the steps of a particular embodiment of the method according to the invention.

FIG. 2 shows a diagram of the steps of a particular embodiment of the method according to the invention, intended for obtaining a lens which allows the modification of the ultrasound beam such that the resulting ultrasound field has a sufficient intensity in a volume which coincides with the treatment area.

A series of nodes 5 and a source point 6 are observed in this diagram. This source point 6 refers to the site where the ultrasound emitter will be centered and the nodes 5 correspond to points representative of the volume intended to be matched with the treatment area.

In this case, the treatment area is intended to be the hippocampus. However, the nodes 5 are situated in the sagittal plane and are separated from one another by a distance of $\lambda/6$, $\lambda$ being the predetermined wavelength. In turn, the source point 6 has been situated close to the sagittal plane of the cranium, in order to check the capacity of the lens to turn the ultrasound beam.

Once the source point 6 and predetermined frequency have been chosen, the following step of the method consists of simulating the emission of spherical waves 7 at the mentioned frequency from each of the nodes 5, creating a simulated wave front resulting from the superposition of the spherical waves 7.

The amplitude of the spherical waves has been chosen based on the distance between the corresponding node and the receiving surface 8, and the phase of each spherical wave has also been chosen based on the distance between the corresponding node and the receiving surface 8.

This simulated wave front is received on the receiving surface 8 which contains the source point 6. The wave front received on this receiving surface 8 is analyzed and in this case, said receiving surface is divided into 1 mm×1 mm pixels. Once the data of the wave front received in each of the pixels of the receiving surface have been collected and processed, it is possible to design a lens surface, by means of methods such as the calculation of the Fabry-Pérot resonator, equivalent heights for each fragment of the lens corresponding to each pixel into which the receiving surface has been divided being chosen, such that a corresponding acoustic hologram can be obtained when said lens is situated in front of a single-element emitter centered on the source point.

When calculating volumetric holograms resulting from the superposition of the waves, pseudo-spectral simulation methods with k-space scatter correction for numerically integrating the linearized constitutive equations of acoustics have been used, as corresponds to cases in which there is a non-homogeneous volume. To resolve this, mesh in which the spatial passage between each of the nodes is $\lambda/6$ is precisely chosen.

Figure 3:
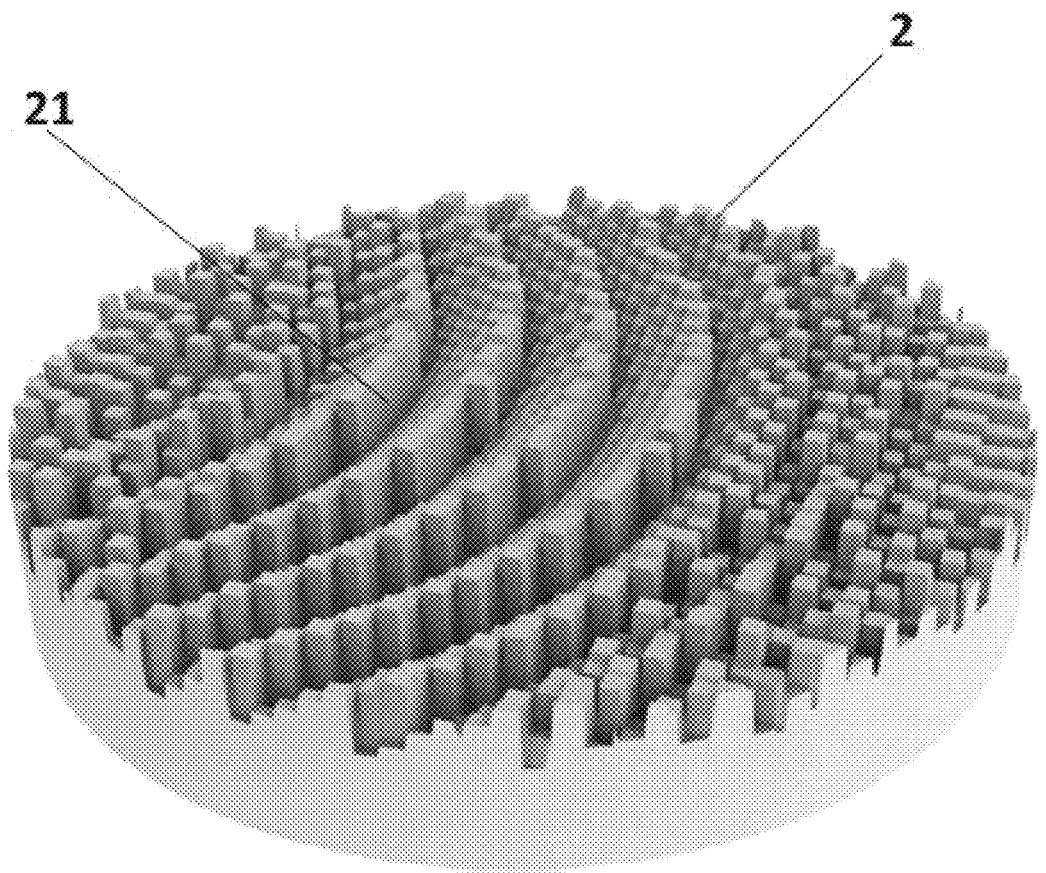
FIG. 3 shows an example of a lens designed by means of a method according to the invention.

FIG. 3 shows an example of a lens 2 designed by means of a method according to the invention.

This lens 2 comprises a plurality of fragments 21 which are responsible for making the necessary corrections in the ultrasound beam to establish the desired pattern, centered on the previously defined treatment area. Each of these fragments 21 corresponds to a column of the previously described model, the base of each column has the size of one pixel and the height of each column corresponds with the previously indicated Fabry-Pérot resonator.

Current three-dimensional printing technology allows the production of lenses of this type, in which very tight production tolerances are required so that the lens thus produced can store all the amplitude and phase information necessary for reproducing the ultrasonic holograms and be incorporated in an ultrasound emission apparatus.

Figure 4:
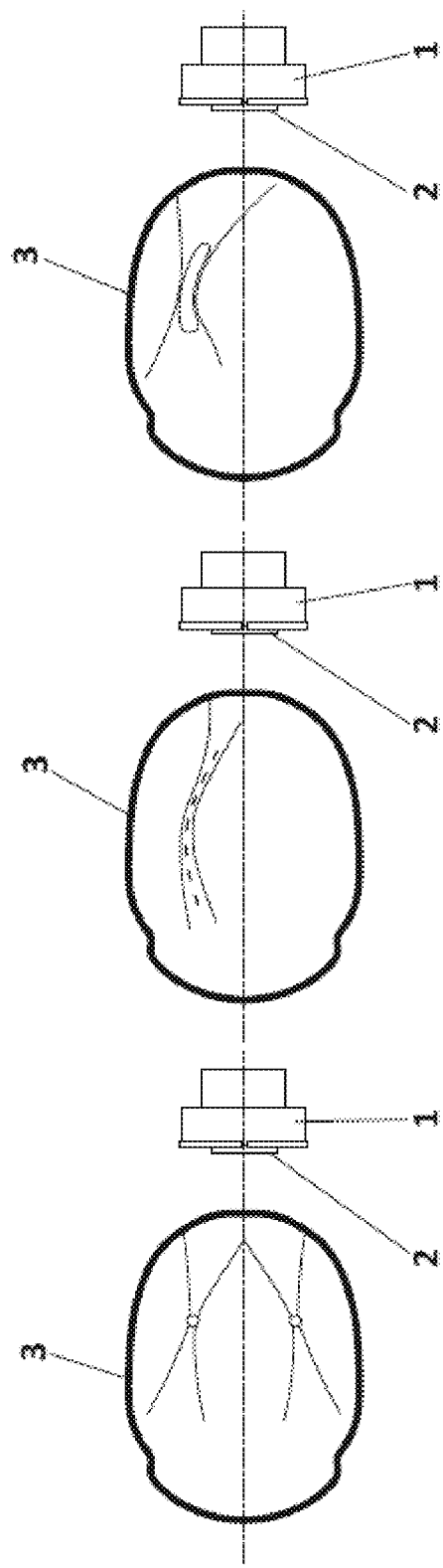
FIGS. 4a to 4c show three possible shapes of the beam generated by the emitter and lens assembly according to the invention.

FIGS. 4a to 4c show three possible shapes of the beam generated by the emitter and lens assembly according to the invention.

FIG. 4a shows a first option in which the beam is concentrated at two points, FIG. 4b shows a second option in which the beam extends along a curved line, and FIG. 4c shows a third option in which the beam covers a previously chosen clearly three-dimensional volume. To achieve each of these distributions, the nodes from which the emission of spherical waves will be simulated will be carefully chosen.

Figure 5:
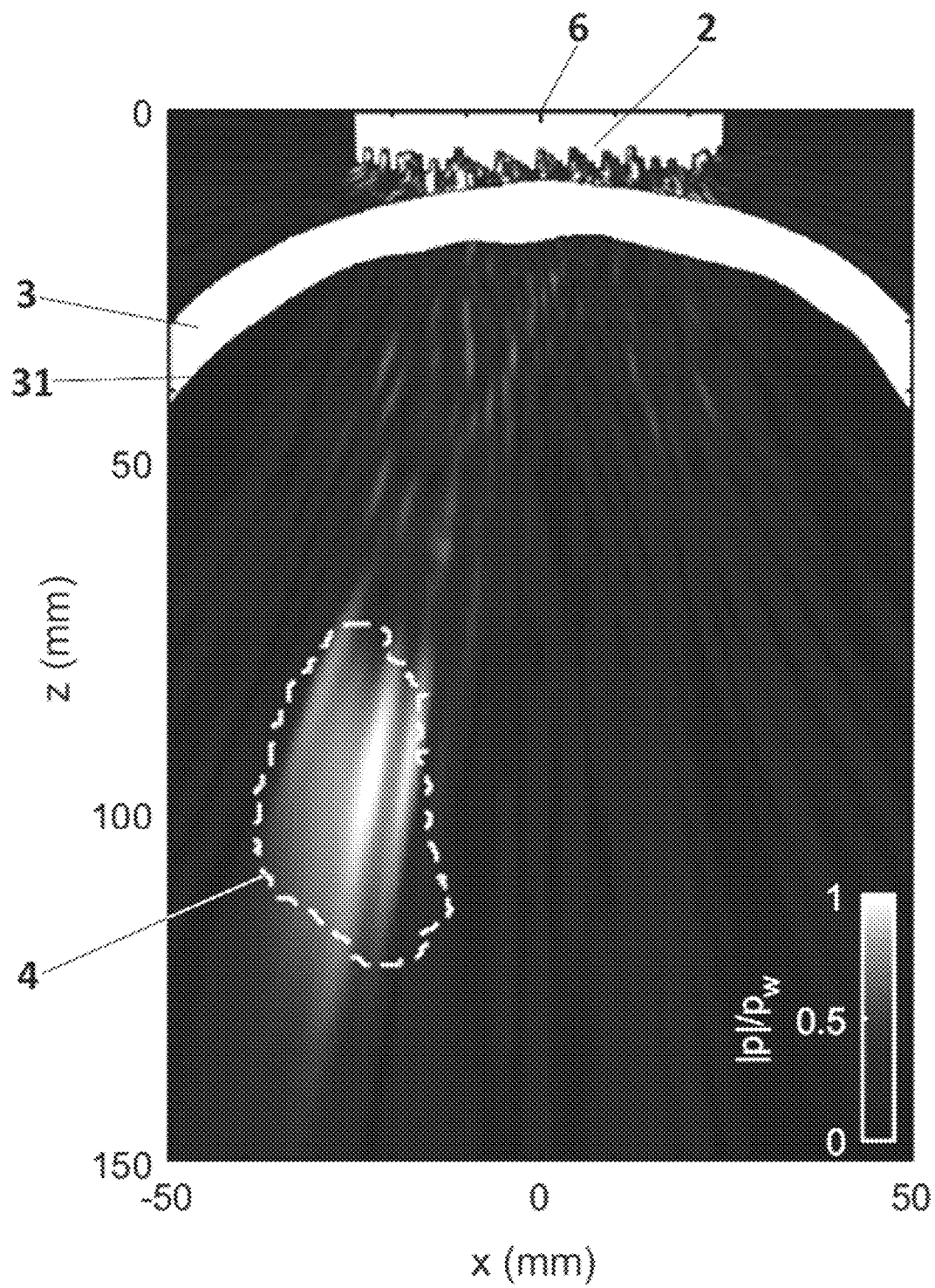
FIG. 5 shows experimental results of a particular embodiment of a method according to the invention.

FIG. 5 shows experimental results of a particular embodiment of a method according to the invention.

In these results, the source point 6 in which the emitter is situated, the position of the lens 2, and the treatment area 4 situated in the cranial cavity 31 enclosed by the cranium 3, can be seen.

As can be observed, the density of ultrasound energy is very high in an area virtually coinciding with the treatment area 4 and is very low in the rest of the cranial cavity 31. The lightest color indicates a higher ultrasound pressure, and this level is considerably higher inside the treatment area 4.

Figure 6A:
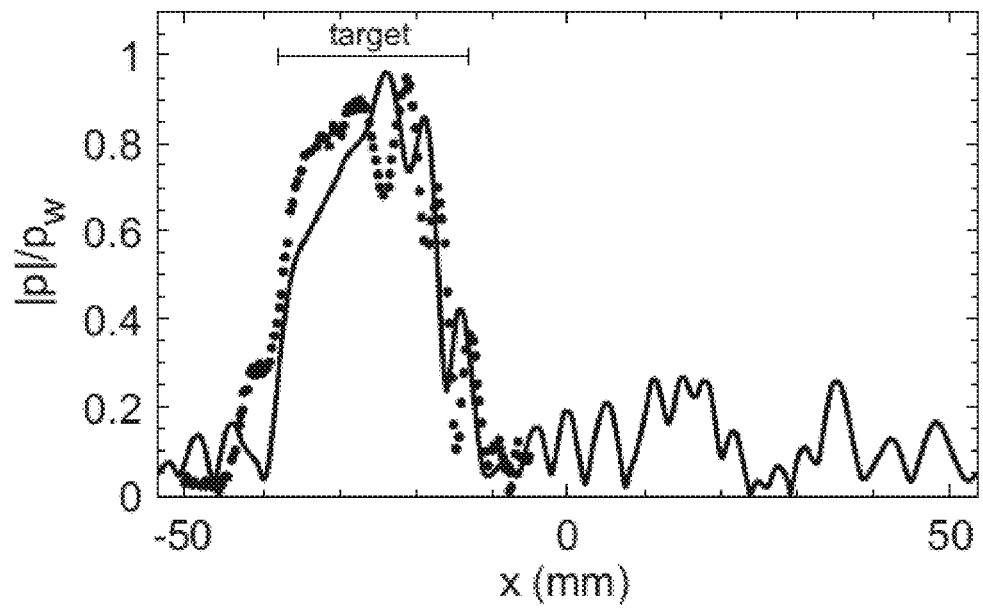
FIGS. 6a and 6b show the graphs related to the experimental results.
Figure 6B:
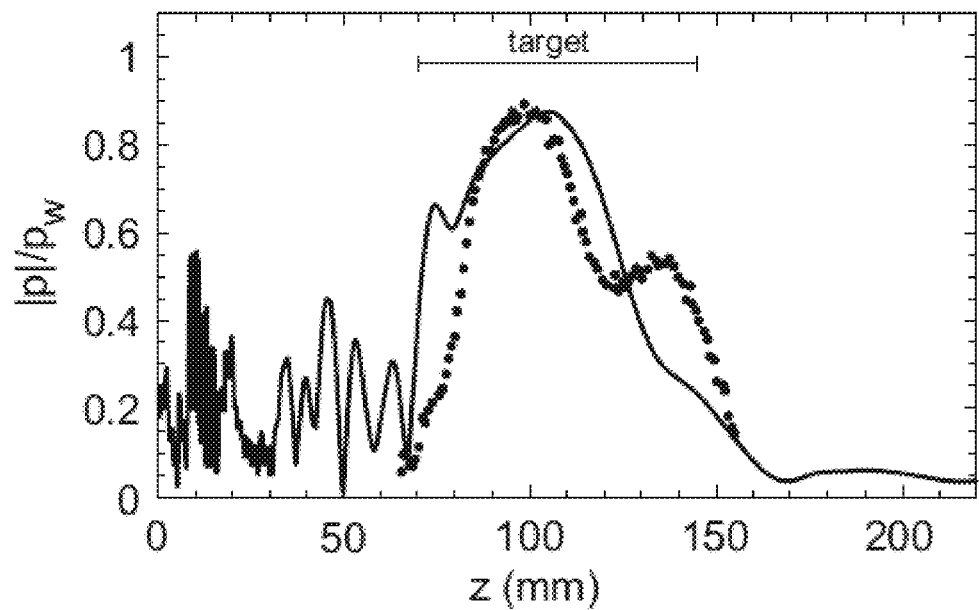

FIGS. 6a and 6b show the graphs confirming this fact. FIG. 6a shows the graph of the amplitude of the pressure waves along the x axis, and FIG. 6b shows the graph of the amplitude of the pressure waves along the z axis. In both graphs, the results of the computer simulation are represented with a continuous line, and the experimental results are represented with a dotted line. It can be observed how the pressure measured in the experimental step notably fits with what has previously been stated about numerical simulation.

The dimensions of the treatment area 4 on both axes are marked by means of a segment with the "target" label. On both axes x, z it can be observed how the intensity of the pressure waves inside said area is much higher than the intensity outside of said area.

In particular embodiments, a piezoelectric material is used for producing the lens object of the invention. This allows obtaining a lens the geometry of which is sensitive to the application of a different electrical voltage to each pixel, therefore the geometry thereof may vary, within limits, once constructed, and even during the working thereof.

The invention claimed is:

1. A method for producing a lens for an ultrasound apparatus, the method comprising the steps of
   providing a barrier tissue model, a soft tissue model surrounded by the barrier tissue model, and a coupling medium model wherein the barrier tissue model presents an acoustic impedance different from that of soft tissue;
   choosing a source point situated in the coupling medium model;
   choosing a predetermined wave frequency and wavelength, the predetermined frequency being comprised between 100 kHz and 20 MHz and the predetermined wavelength being determined by the predetermined frequency and a velocity of propagation of the wave in the coupling medium model;
   providing a treatment volume situated inside the barrier tissue model;
   providing a plurality of nodes distributed inside the treatment volume;
   simulating the emission of a spherical wave from each of the nodes of the plurality of nodes, creating a simulated wave front resulting from the superposition of the spherical waves, each spherical wave requiring an amplitude and a phase, there being at least two nodes with different amplitudes or phases, each spherical wave having the predetermined frequency;
   receiving the simulated wave front on a receiving surface which contains the source point;
   processing the results received on the receiving surface;
   on the basis of the processed results, designing a holographic lens surface which can generate a wave pattern equivalent to the simulated, time-reversed, wave front when it receives a wave from a planar, single-element emitter situated at the source point with the predetermined wave frequency and wavelengths.

2. The method according to claim 1, wherein the plurality of nodes are volumetrically distributed inside the treatment volume.

3. The method according to claim 1, wherein the step of processing the results received comprises dividing the receiving surface into pixels and analyzing the amplitude and phase of the wave received in each pixel.

4. The method according to claim 3, wherein the pixel size depends on the predetermined wavelength, and in particular the size of each pixel is a square with $5\lambda/6$ of side, $\lambda$ being the predetermined wavelength.

5. The method according to claim 3, wherein each pixel of the receiving surface is considered as a Fabry-Pérot type resonator which can resonate longitudinally, giving rise to a fragment of the lens, and in the step of designing the holographic lens surface equivalent heights are chosen for each fragment of the lens based on the amplitude and phase of the wave received in each pixel of the receiving surface.

6. The method according to claim 5, wherein the amplitude or the phase of each spherical wave is a free parameter, and the method includes the iteration of the steps of simulating the emission of spherical waves, receiving the simulated wave front, and processing the results until obtaining by iteration length values of the Fabry-Pérot resonator which give rise to a distribution of sound energy in the treatment volume which exceeds a pre-established target.

7. The method according to claim 1, wherein in the step of designing the lens a time reversal type method is used.

8. The method according to claim 1, wherein any pair of nodes is separated from one another by a distance of less than $\lambda/2$, $\lambda$ being the predetermined wavelength.

9. The method according to claim 1, wherein in the step of simulating the emission of spherical waves the amplitude of at least two spherical waves is different.

10. The method according to claim 9, wherein an amplitude is imposed on each spherical wave which depends on the distance between the node emitting said spherical wave and the receiving surface.

11. The method according to claim 9, wherein the amplitude of each spherical wave is a free parameter, and the method includes the iteration of the steps of simulating the emission of spherical waves, receiving the simulated wave front, and processing the results until obtaining by iteration amplitude values for each spherical wave which give rise to a distribution of sound energy in the treatment volume which exceeds a pre-established target.

12. The method according to claim 1, wherein in the step of simulating the emission of spherical waves the phase of at least two spherical waves is different.

13. The method according to claim 12, wherein a phase is imposed on each spherical wave which depends on the distance between the node emitting said spherical wave and the receiving surface.

14. The method according to claim 12, wherein the phase of each spherical wave is a free parameter, and the method includes the iteration of the steps of simulating the emission of spherical waves, receiving the simulated wave front, and processing the results until obtaining by iteration phase values for each spherical wave which give rise to a distribution of sound energy in the treatment volume which exceeds a pre-established target.

15. The method according to claim 1, further comprising the step of three-dimensionally producing the design of the lens obtained in the corresponding step.

16. The method according to claim 15, wherein a piezoelectric material is used in the step of producing the lens.

17. An apparatus comprising a lens produced by the method according to claim 1.

18. The apparatus according to claim 17, configured for carrying out a high-intensity focused ultrasound method.

19. The method according to claim 1, wherein the barrier tissue model is a bone tissue model.

\* \* \* \* \*